United States Patent [19]

Hirose

[11] Patent Number: 5,407,545
[45] Date of Patent: Apr. 18, 1995

[54] METHOD FOR MEASURING SAMPLE BY ENZYME ELECTRODES

[75] Inventor: Kazunori Hirose, Kyoto, Japan

[73] Assignee: Kyoto Daiichi Kagaku Co., Ltd., Kyoto, Japan

[21] Appl. No.: 231,665

[22] Filed: Apr. 25, 1994

[30] Foreign Application Priority Data

Apr. 30, 1993 [JP] Japan .................. 5-104104

[51] Int. Cl.$^6$ .............................. G01N 27/26
[52] U.S. Cl. .................. 204/153.12; 204/153.1
[58] Field of Search ............. 204/153.12, 153.1; 435/4, 14, 10

[56] References Cited

U.S. PATENT DOCUMENTS

| | | | |
|---|---|---|---|
| 4,767,994 | 8/1988 | Hopkins et al. | 204/406 |
| 5,312,528 | 5/1994 | Hoogendijk | 204/153.1 |
| 5,320,939 | 6/1994 | Hashizume et al. | 204/403 |

FOREIGN PATENT DOCUMENTS

| | | |
|---|---|---|
| 207264 | 2/1984 | European Pat. Off. . |
| 0286118 | 10/1988 | European Pat. Off. . |
| 0407992 | 1/1991 | European Pat. Off. . |
| 62-294954 | 12/1987 | Japan . |

OTHER PUBLICATIONS

Patent Abstracts of Japan, vol. 007, No. 026 no month or year available.
Database WPI, Section Ch, Week 8302, Derwent Publications Ltd., London no month or year available.

Primary Examiner—John Niebling
Assistant Examiner—Bruce F. Bell
Attorney, Agent, or Firm—Birch, Stewart, Kolasch & Birch

[57] ABSTRACT

A buffer solution is charged in a reaction container so that enzyme electrodes can be immersed in the buffer solution. Current values between the enzyme electrodes, to which a voltage is applied, are sampled at predetermined-time intervals. A decreasing curve of current is predicted on the basis of the sampled current values. A sample is injected in said buffer solution at an early time before the current between enzyme electrodes become stable, whereby oxidation reaction of a specified component of the sample is caused. A current value $I_1$ between enzyme electrodes is measured and simultaneously a current value $T_2$ on the decreasing curve is obtained at a point that a predetermined time passes from the sample injection point to obtain a current increase from the sample injection on the basis of a difference of the current values $I_1$ and $I_2$. A quantity of the specified component of the sample is obtained on the basis of the current increase.

11 Claims, 3 Drawing Sheets

METHOD FOR MEASURING SAMPLE BY ENZYME ELECTRODES

BACKGROUND OF THE INVENTION

1. Field of the Invention

The present invention relates to a method for measuring sample by enzyme electrodes, more particularly to a method for measuring a specified component in a body fluid, for example, blood, blood plasma, urine and so on by using the enzyme electrodes.

2. Description of the Prior Art

Recently enzyme electrodes have been employed for measuring a specified component in a body fluid, e.g. blood. For example, in a quantitative analysis of glucose, a glucose sensor which is formed by fixing a membrane of glucose oxidizing enzyme on the surfaces of hydrogen peroxide electrodes is employed. After a measurement voltage is applied to the electrodes of glucose sensor, buffer solution is charged in a reaction container so that the ends of glucose sensor can be immersed. An electric current between the electrodes becomes stable and then a sample is injected in the buffer solution. The quantity of glucose can be obtained by measuring the change in the electric current between electrodes from the time point of sample injection.

Since it has taken 1–5 minutes for the electric current to become stable after charging the buffer solution, it was necessary to wait for long time to commence the injection of sample and the measurement, which resulted in a greatly inefficient operation.

A method for stabilizing early electric current between enzyme electrodes has been proposed in Japanese patent laid-open publication No. 62-294954. In this method, a higher voltage than measurement voltage is applied to the enzyme electrodes and then the measurement voltage is applied thereto. According to the method, although the stable point of the current becomes a little early, it needs to wait for the current to become stable nevertheless.

SUMMARY OF THE INVENTION

The present invention has been developed to substantially eliminate the above-described disadvantages.

It is an object of the present invention to provide a method for measuring sample by enzyme electrodes in which it is possible to commence a measurement of sample early and to improve the efficiency of operation.

In order to achieve the aforementioned object, there is provided a method for measuring sample by enzyme electrodes comprising the following steps of: charging a buffer solution in a reaction container so that the enzyme electrodes can be immersed in the buffer solution; sampling current values between enzyme electrodes, to which a voltage is applied, at predetermined-time intervals; predicting a decreasing curve of current on the basis of the current values; injecting a sample in the buffer solution at an early time before the current between enzyme electrodes become stable, whereby oxidation reaction of a specified component of the sample is caused; measuring a current value $I_1$ between the enzyme electrodes and simultaneously obtaining a current value $I_2$ on the decreasing curve at a point that a predetermined time passes from the sample injection point to obtain a current increase from the sample injection on the basis of a difference of the current values $I_1$ and $I_2$; and obtaining a quantity of the specified component of the sample on the basis of said current increase.

Another embodiment of the method of the present invention comprises the following steps of: charging a buffer solution in a reaction container so that the enzyme electrodes can be immersed in the buffer solution; sampling current values between the enzyme electrodes, to which a voltage is applied, at predetermined-time intervals; predicting a decreasing curve of current on the basis of the current values to obtain a differential decreasing curve by differentiating the decreasing curve; injecting a sample in the buffer solution at an early time before the current between enzyme electrodes become stable, whereby oxidation reaction of a specified component of the sample is caused; obtaining a differential reaction curve by differentiating a reaction curve of current measured under the oxidation reaction; obtaining a differential current value $dI_1$ on the differential reaction curve and a differential current value $dI_2$ on the differential decreasing curve at a peak point of the differential reaction curve to obtain a current increase from the sample injection on the basis of a difference of the differential current values $dI_1$ and $dI_2$; and obtaining a quantity of the specified component of the sample on the basis of the current increase.

In the preferred embodiment, the decreasing curve may be predicted by a least square method. The step of predicting a decreasing curve of current may be prosecuted at every time of measurement of each sample.

The sample may be a blood, a blood serum, a blood plasma, a urine. The specified component may be a glucose, a uric acid, a lactic acid.

BRIEF DESCRIPTION OF THE DRAWINGS

Further objects and advantages of the present invention will become clear from the following description taken in conjunction with the preferred embodiments thereof with reference to the accompanying drawings.

DETAILED DESCRIPTION OF THE PREFERRED EMBODIMENTS

Figure 1:
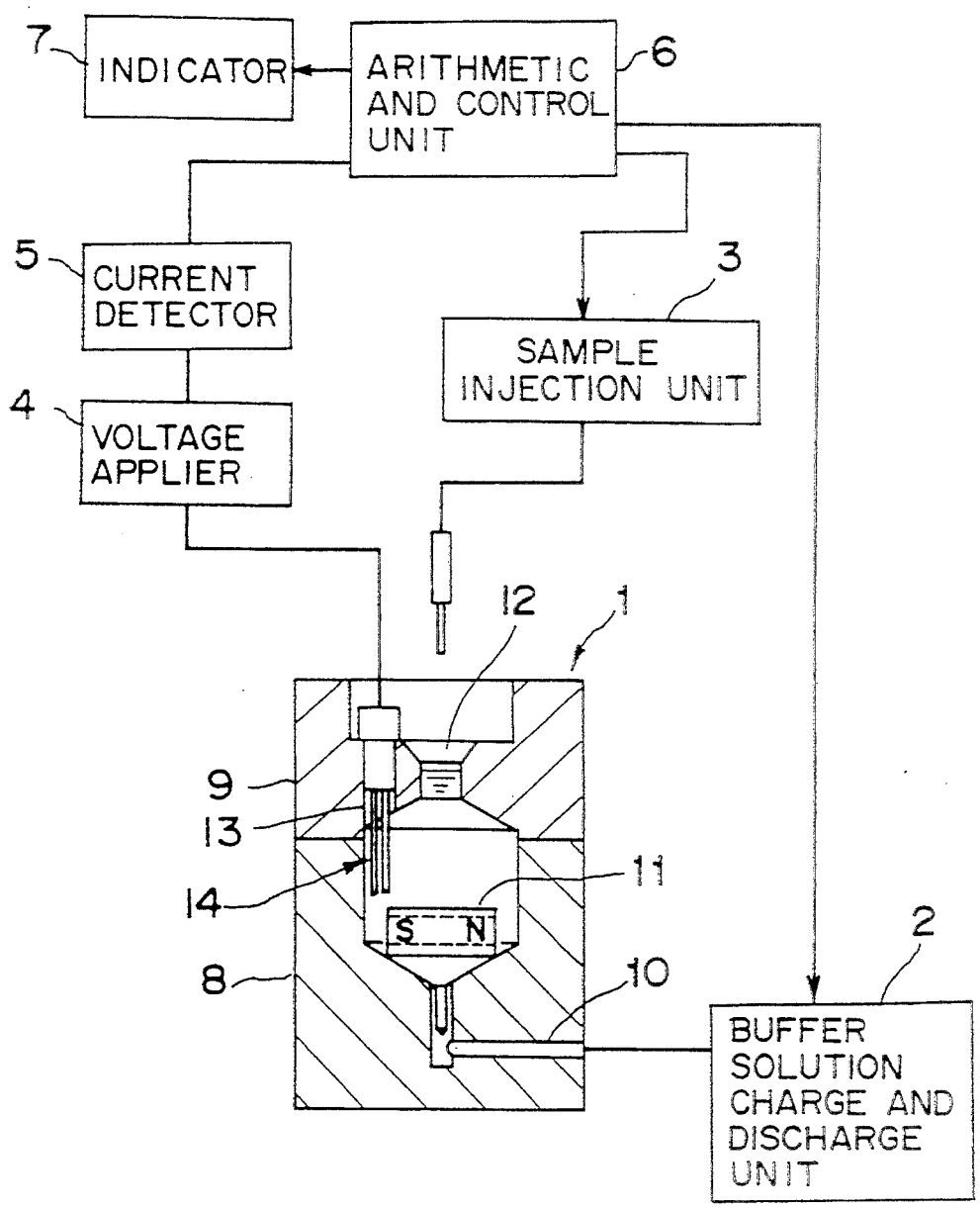
FIG. 1 is a sectional drawing of the reaction container and a block diagram of the apparatus for the working of the method according to the present invention.

FIG. 1 shows an apparatus for working a method for measuring a glucose in a blood sample according to the present invention. The apparatus comprises a reaction container 1, a buffer solution charge and discharge unit 2, a sample injection unit 3, a voltage applier 4, current detector 5, arithmetic and control unit 6, and indicator 7.

The reaction container 1 is constituted by a lower container 8 and an upper container 9. In the bottom of the lower container 8 is formed a charge and discharge port 10 for buffer solution. Inside of the lower container 8 is contained a stirrer 11 having a shape of top, which is capable of rotating according to the rotation of a magnet not shown so as to stir the buffer solution. The upper container 9 is installed on the lower container 8 so that an internal space can be made. In the bottom of the upper container 9 are formed a opening 12 for injecting the sample and a hole 13 for inserting a glucose sensor 14. The glucose sensor 14 comprises enzyme electrodes. The glucose sensor 14 is fixed on the upper container 9 so that the ends of enzyme electrodes are immersed in the buffer solution charged in the reaction container 1.

The buffer solution charge and discharge unit 2 charges a predetermined quantity of buffer solution into the reaction container 1 through the charge and discharge port 10 and discharges the reaction liquid in the container 1 through the port 10 after finishing measurement.

The sample injection unit 3 sucks the sample contained in a sample bottle not shown to inject it into the inside of the reaction container 1 through the opening 12.

The voltage applier 4 comprises an electric circuit which applies a measurement voltage of 0.6V to the electrodes of the glucose sensor 14.

The current detector 5 detects the electric current passing between the electrodes of glucose sensor 14 to which the voltage is applied by the voltage applier 4.

The arithmetic and control unit 6 controls the operation of the buffer solution charge and discharge unit 2 and the sample injection unit 3, obtains the quantity of glucose in the blood sample on the basis of the detecting signal from the voltage applier 5, and indicates it on the indicator 7.

Figure 3:
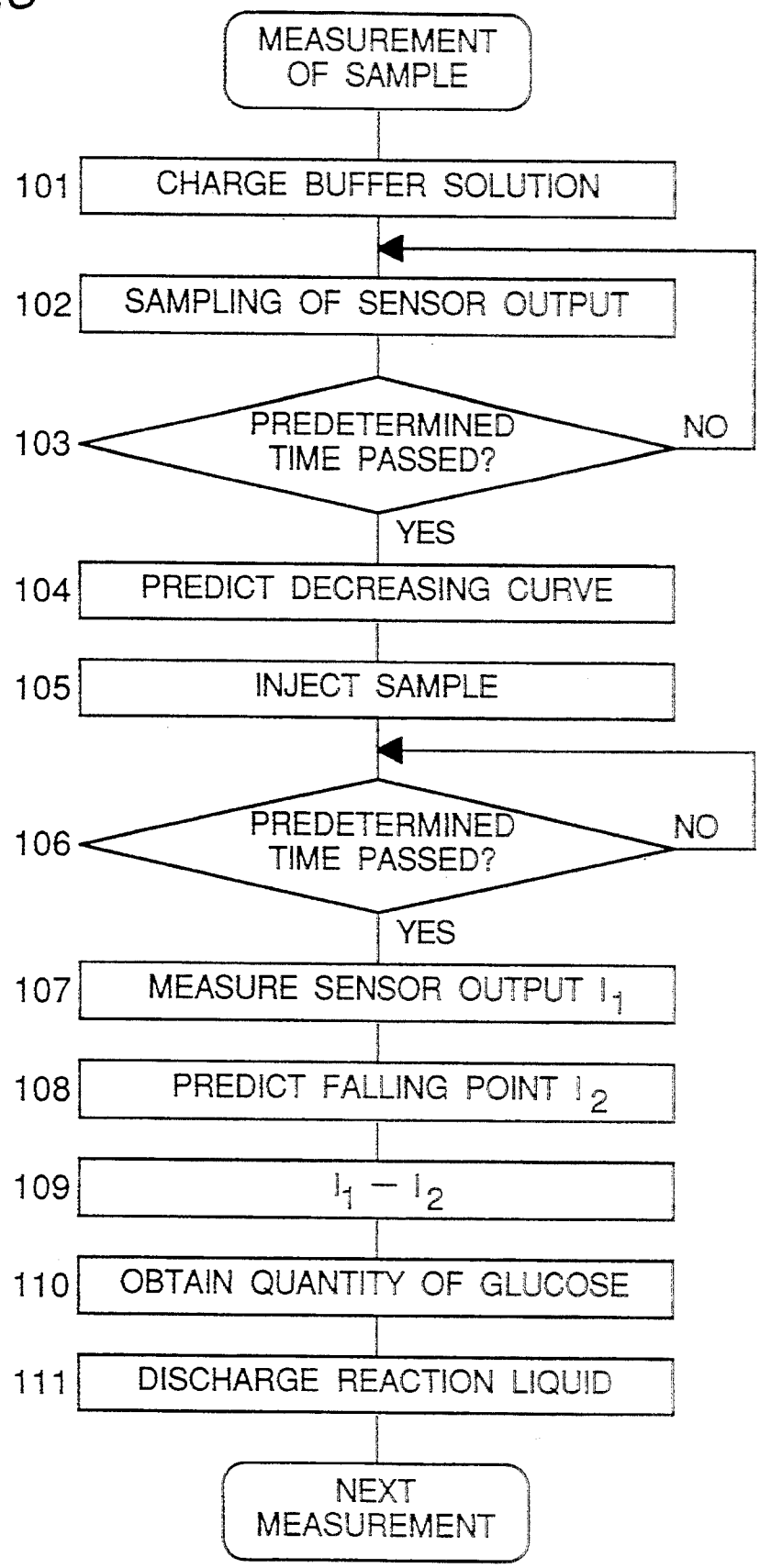
FIG. 3 is a flow chart showing the procedure of measuring method according to the present invention.

The operation of arithmetic and control unit 6 of said apparatus constituted as described above for measuring the quantity of glucose in the blood will be explained hereinafter in accordance with the flow chart as shown in FIG. 3.

First of all, in the Step 101, the buffer solution is charged into the reaction container 1 by the operation of buffer solution charge and discharge unit 2. Referring to the FIG. 2, the charging point of buffer solution is defined as $t_1$. An inrush current passes between the electrodes of the glucose sensor 14 at the point $t_1$ and decreases gradually to become stable. In the conventional method the measurement have been commenced by injecting a sample at the point $t_2'$ that the sensor output would be stable, while in the embodiment of the present invention the measurement is commenced at an early point $t_2$ before the sensor output will become stable.

The arithmetic and control unit 6 takes samples of the electric current value detected by the current detector 5 at predetermined-time intervals in Step 102. The sampling is continued until a predetermined time from the point $t_1$ passes in Step 104. A decreasing curve of the electric current is predicted by a least square method in Step 104. At the point $t_2$ that the predetermined time from the point $t_1$ passes, the blood sample is injected into the reaction container 1 through the opening 12 by the operation of sample injection unit 3 in Step 105. The β-D-glucose contained in the blood sample is oxidized under the activity of glucose oxidizing enzyme of glucose sensor 14 to change into D-gluconic acid and to generate hydrogen peroxide solution. As the hydrogen peroxide is converted into electric signal by the hydrogen peroxide electrodes of glucose sensor 14, the sensor output varies in accordance with the changes in the quantity of hydrogen peroxide, that is, the quantity of glucose.

Figure 2:
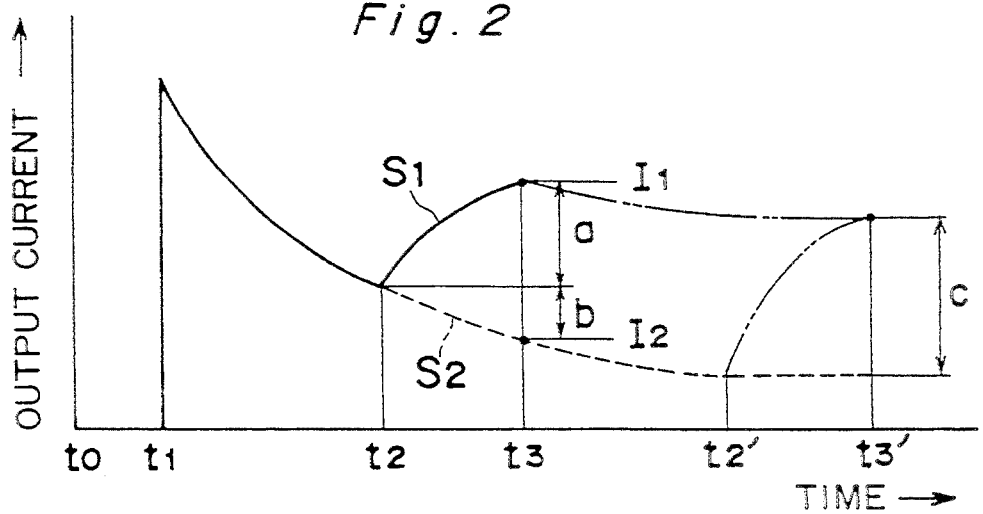
FIG. 2 is a graph showing the change in the current between enzyme electrodes.

This will be described more concretely hereinafter with reference to the FIG. 2. At the sample injection point of $t_2$ the sensor output begins to increase to become stable at a constant value. A stable point $t_3$ of reaction curve $S_1$ from the sample injection point of $t_2$ may be determined by experience. The sum (a+b) of the increasing quantity (a) of the sensor output at the stable point $t_3$ from the point $t_2$ along the reaction curve $S_1$ and the falling quantity (b) of the sensor output at the stable point $t_3$ from the point $t_2$ along the decreasing curve $S_2$ is identical with the increasing quantity (c) of the sensor output in case that the measurement is commenced at the stable point $t_2'$ of the decreasing curve $S_2$ of inrush current. The value of (a+b) which corresponds to the quantity of reaction is obtained by calculating the difference between the sensor output $I_1$ at the stable point $t_3$ of the reaction curve $S_1$ and the sensor output $I_2$ at the falling point, which corresponds to the above point $t_3$, of the decreasing curve $S_2$.

In this embodiment, after waiting for the predetermined time to pass from the sample injection point $t_2$ in Step 106, at the point $t_3$ that the predetermined time passes the arithmetic and control unit 6 reads out the sensor output $I_1$ in Step 107 and obtains the current $I_2$ at the falling point on the basis of the decreasing curve $S_2$ in Step 108. Then, the unit 6 calculates $(I_1-I_2)$ in Step 109, obtains the quantity of glucose in Step 110, and indicates the result on the indicator 7. After the reaction liquid in the reaction container 1 is discharged by the operation of buffer solution charge and discharge unit 2 in Step 111, the measurement of next sample is commenced.

As described above, the measurement of sample according to the present invention can be commenced at early point without waiting for the stability of decrease of sensor output from the voltage applying point $t_1$, which causes the measurement to terminate at earlier point $t_3$ than the point $t_3'$ at which the measurement according to the conventional method terminates.

In case of continuous measurement of a large number of samples, since the reaction liquid at the previous measurement remains on the internal surfaces of the reaction container 1 or in the spaces between the reaction container 1 and stirrer 11, there may be a possibility that such remaining reaction liquid contaminates the buffer solution or sample at the next measurement. If the decreasing curve predicted in the previous measurement procedure is used as it was in spite of such a contamination, the measurement results will become inaccurate. Therefore it is preferable to update the decreasing curve at each time of measurement of new sample.

In case that there is no possibility of contamination because the reaction container 1 is cleaned entirely after measuring the sample, the decreasing curve predicted at the first measurement of the sample can be used at the subsequent measurement.

Figure 4:
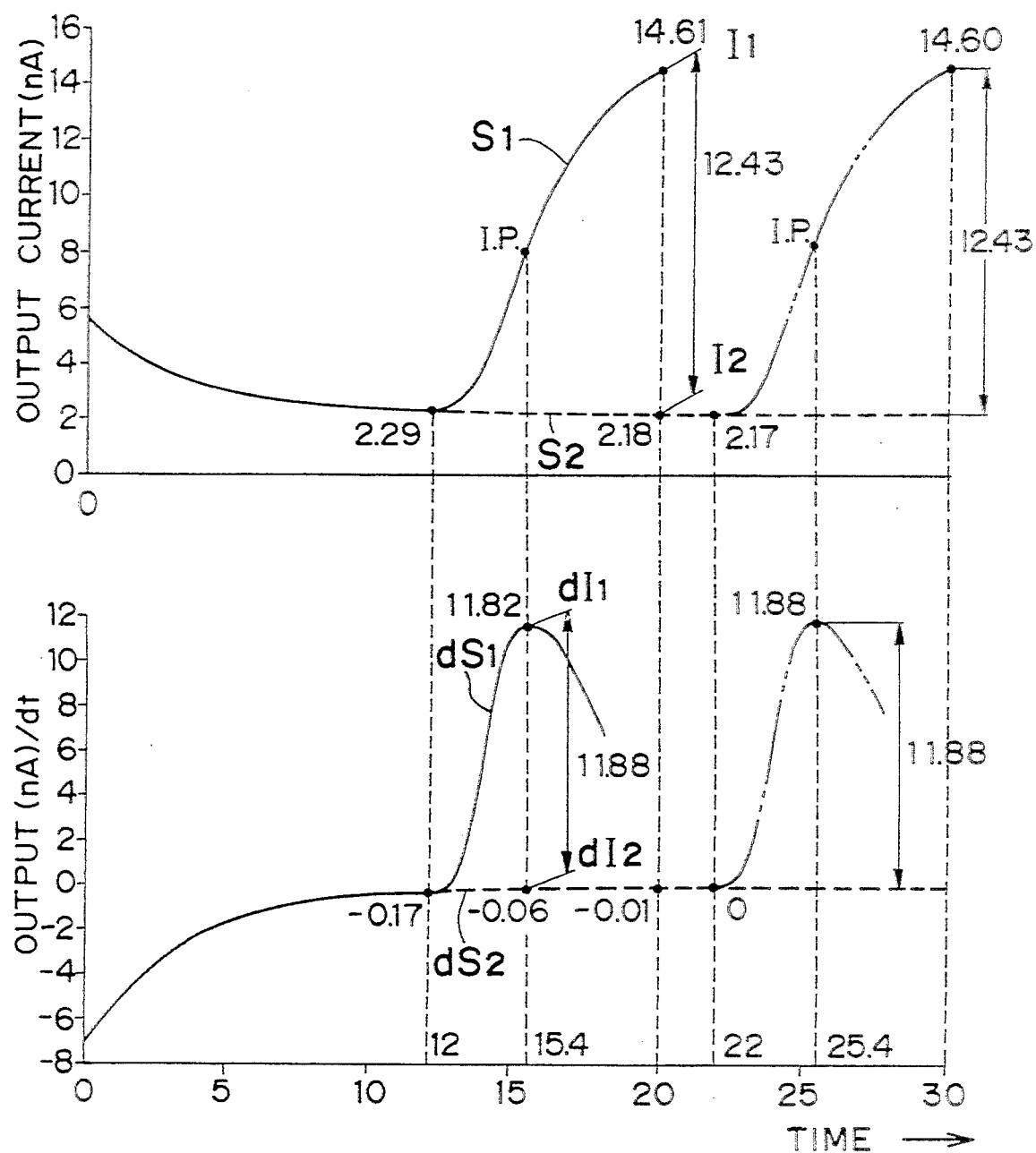
FIG. 4 is a graph showing output current curve and its differential curve based on experimental data.

The upper graph in FIG. 4 shows experimental data of current between enzyme electrodes. It needed 22 seconds until the stabilization of inrush current after applying a voltage. At the conventional method, the sample was injected at a point of 22 seconds and the measurement was completed at a point of 30 seconds. According to the present invention, the sample was injected at a point of 12 seconds and the measurement was completed at a point of 20 seconds.

The lower graph in FIG. 4 shows a differential reaction curve $dS_1$ and a differential decreasing curve $dS_2$ which are obtained by differentiating the reaction curve $S_1$ and the decreasing curve $S_2$ in the upper graph respectively. The current increase (12.43 nA) from the sample injection point (12 seconds) may be obtained by integrating the differential reaction curve $dS_1$. However, it is known that the current increase (12.43 nA) from the sample injection point at a stable point on the reaction curve $S_1$ is proportional to the differential current increase (11.88 nA/dt) from the sample injection point at a peak point on the differential reaction curve $dS_1$, that is, an inflection point (I.P.) on the reaction curve $S_1$.

Therefore, after obtaining a difference between a differential current value $dI_1$ (11.82 nA/dt) on the differential reaction curve $dS_1$ and a differential current value $dI_2$ (−0.06 nA/dt) on the differential decreasing curve $dS_2$ at the peak point (15.4 seconds) on the differential reaction curve $dS_1$, the current increase from the sample injection point (12 seconds) can be obtained from the difference by a proportional calculation. According to this method, the completion of measurement will be shortened at a point of 15.4 seconds.

As is clear from the above description, according to the present invention, since the sample can be injected so as to commence the measurement before the current of enzyme electrodes become in stable after charging the buffer solution, the measurement time per a sample is shortened, which causes the improvement of operational efficiency.

In addition, according to the another aspect of the invention, the decreasing curve is predicted at each time of measurement of sample. Even if the new sample is contaminated by the previous sample which remains in the reaction container at the time of previous measurement, the decreasing curve is predicted and updated at the contaminated condition. Therefore the new sample will be measured accurately without being influenced by the contamination.

Although the present invention has been fully described by way of the examples with reference to the accompanying drawing, it is to be noted here that various changes and modifications will be apparent to those skilled in the art. Therefore, unless such changes and modifications otherwise depart from the spirit and scope of the present invention, they should be construed as being included therein.

What is claimed is:

1. A method for measuring sample by enzyme electrodes comprising the following steps of:
    charging a buffer solution in a reaction container so that said enzyme electrodes can be immersed in said buffer solution;
    sampling current values between said enzyme electrodes, to which a voltage is applied, at set-time intervals;
    predicting a decreasing curve of current on the basis of said current values;
    injecting a sample in said buffer solution at an early time before said current between enzyme electrodes become stable, whereby oxidation reaction of a specified component of said sample is caused;
    measuring a current value $I_1$ between said enzyme electrodes and simultaneously obtaining a current value $I_2$ on said decreasing curve at a point that a set time passes from said sample injection point to obtain a current increase from said sample injection on the basis of a difference of said current values $I_1$ and $I_2$; and
    obtaining a quantity of said specified component of said sample on the basis of said current increase.

2. A method for measuring sample by enzyme electrodes comprising the following steps of:
    charging a buffer solution in a reaction container so that said enzyme electrodes can be immersed in said buffer solution;
    sampling current values between said enzyme electrodes, to which a voltage is applied, at set-time intervals;
    predicting a decreasing curve of current on the basis of said current values to obtain a differential decreasing curve by differentiating said decreasing curve;
    injecting a sample in said buffer solution at an early time before said current between enzyme electrodes become stable, whereby oxidation reaction of a specified component of said sample is caused;
    obtaining a differential reaction curve by differentiating a reaction curve of current measured under said oxidation reaction;
    obtaining a differential current value $dI_1$ on said differential reaction curve and a differential current value $dI_2$ on said differential decreasing curve at a peak point of said differential reaction curve to obtain a current increase from said sample injection on the basis of a difference of said differential current values $dI_1$ and $dI_2$; and
    obtaining a quantity of said specified component of said sample on the basis of said current increase.

3. A method according to claim 1 or 2, wherein said decreasing curve is predicted by a least square method.

4. A method according to claim 1 or 2, wherein said step of predicting a decreasing curve of current is prosecuted at every time of measurement of each sample.

5. A method according to claim 1 or 2, wherein said sample is a blood.

6. A method according to claim 1 or 2, wherein said sample is a blood serum.

7. A method according to claim 1 or 2, wherein said sample is a blood plasma.

8. A method according to claim 1 or 2, wherein said sample is a urine.

9. A method according to claim 1 or 2, wherein said specified component is a glucose.

10. A method according to claim 1 or 2, wherein said specified component is a uric acid.

11. A method according to claim 1 or 2, wherein said sample is a lactic acid.

* * * * *